(12) United States Patent
Bertozzi et al.

(10) Patent No.: US 6,936,701 B2
(45) Date of Patent: *Aug. 30, 2005

(54) GLYCOCONJUGATES AND METHODS

(75) Inventors: Carolyn Bertozzi, Albany, CA (US);
Kevin J. Yarema, Albany, CA (US);
Lara K. Mahal, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 195 days.

This patent is subject to a terminal disclaimer.

(21) Appl. No.: 10/254,180

(22) Filed: Sep. 24, 2002

(65) Prior Publication Data

US 2003/0049721 A1 Mar. 13, 2003

Related U.S. Application Data

(60) Continuation of application No. 09/571,527, filed on May 16, 2000, now Pat. No. 6,458,937, which is a division of application No. 08/856,865, filed on May 15, 1997, now Pat. No. 6,075,134.

(51) Int. Cl.[7] .................... A61K 39/385; C07H 15/04; C07H 15/12
(52) U.S. Cl. .................. 536/17.2; 536/124; 424/194.1; 424/194.11
(58) Field of Search .................. 536/17.2, 124; 424/194.1, 194.11

(56) References Cited

U.S. PATENT DOCUMENTS 5,767,378 A * 6/1998 Bojsen et al. ............ 800/317.2
6,075,134 A * 6/2000 Bertozzi et al. ............ 536/17.2

OTHER PUBLICATIONS

Keppler, O. T. et al "Biosynthetic modulation of sialic acid–dependent virus–receptor interction of two primate polyoma viruses" Biol. Chem. (1995) vol 270, no 3, pp 1308–1314.*

* cited by examiner

Primary Examiner—Leigh C. Maier
(74) Attorney, Agent, or Firm—Peters, Verny, Jones, Schmitt & Aston, LLP; David J. Aston

(57) ABSTRACT

Methods for making the functionalized glycoconjugates include (a) contacting a cell with a first monosaccharide, and (b) incubating the cell under conditions whereby the cell (i) internalizes the first monosaccharide, (ii) biochemically processes the first monosaccharide into a second saccharide, (iii) conjugates the saccharide to a carrier to form a glycoconjugate, and (iv) extracellularly expresses the glycoconjugate to form an extracellular glycoconjugate comprising a selectively reactive functional group. Methods for forming products at a cell further comprise contacting the functional group of the extracellularly expressed glycoconjugate with an agent which selectively reacts with the functional group to form a product. Subject compositions include cyto-compatible monosaccharides comprising a nitrogen or ether linked functional group selectively reactive at a cell surface and compositions and cells comprising such saccharides.

18 Claims, 12 Drawing Sheets

A

B

R1 IS ALKYL, ARYL OR HETEROATOM-CONTAINING GROUP

ManLev

R1 AND R2 ARE ALKYL, ARYL OR HETEROATOM-CONTAINING GROUPS

R1 AND R2 ARE ALKYL, ARYL OR HETEROATOM-CONTAINING GROUPS

R1 AND R2 ARE H OR ALKYL, ARYL OR HETEROATOM-CONTAINING GROUPS.

$R_1$ and $R_2$ are alkyl or aryl groups, or heteroatom-containing groups. $R_3$ and $R_4$ are O, S or $H_2$.

$R_1$ and $R_2$ are alkyl or aryl groups, or heteroatom-containing groups. $R_3$ is O, S or $H_2$.

Specific examples:

6-N-levulinamido fucose (FucLev)

GLYCOCONJUGATES AND METHODS

This is a continuation application of U.S. application Ser. No. 09/571,527, filed on May 16, 2000, now U.S. Pat. No. 6,458,937, which is a divisional of U.S. application Ser. No. 08/856,865 filed on May 15, 1997, now U.S. Pat. No. 6,075,134.

The research carried out in the subject application was supported in part by grants from the Department of Energy (Contract No. DE-AC03-76SF00098). The government may have rights in any patent issuing on this application.

INTRODUCTION

1. Field of the Invention

The invention relates to functionalized saccharides and methods of making and using such saccharides.

2. Background of the Invention

The early diagnosis and treatment of cancer, a family of diseases that affects one in three Americans, continues to present a major challenge (1). While primary tumors can be removed surgically, by the time they are identified, metastatic cells may have spread throughout the body resulting in the lethal growth of tumors in secondary sites. As a result, most treatment protocols involve the additional use of chemotherapeutics, many of which are characterized by severe toxic side effects. These problems have motivated the search for cancer-cell specific agents capable of facilitating the early diagnosis of tumors (i.e., before metastases have developed) and targeting the toxic effects of drugs to cancer cells and away from normal cells. A central feature of these efforts is the identification of cell-surface antigens that are specific to cancer cells. Several such antigens have been identified and, likewise, some progress has been achieved using monoclonal antibodies (mAbs) as delivery agents for drugs ("immunotoxins") (2) and diagnostic probes ("immunodiagnostics") (3). Unfortunately, the heterogeneity of cancer-associated epitopes has necessitated laborious and cumbersome mAb preparation for each of the myriad of different cancer-associated antigens (4,5). Furthermore, the murine-based mAbs in common usage have proven to be immunogenic in human patients (6) and attempts to "humanize" such mAbs have not yet reached maturity (7). A particularly refractory problem is the development of resistant cells that are able to mask or downregulate the targeted antigens (4,8). Thus, alternative approaches are urgently needed for selective cancer cell targeting.

The composition of cell surface carbohydrates is dramatically altered in many epithelial and blood-derived cancers. Alterations in cancer-associated cell surface carbohydrate structures can be divided into two broad categories: a) increased levels and inappropriate expression of normal oligosaccharide epitopes and b) expression of novel carbohydrate moieties that do not normally occur on healthy cells. The major antigen families associated with transformed cells are the sialyl Lewis a, sialyl Lewis x, Lewis y, A and Tn-related oligosaccharides (4). A common feature of these antigens is that each contains one or more terminal sialic acid or fucose residues, and the Lewis antigens contain both. The overexpression of sialic acid and fucose residues is highly correlated with increased metastatic potential in several cancers with the greatest impact on human health including gastric, uterine endometrial, colonic, epithelial, pancreatic, bladder, liver, lung, prostate and breast cancers as well as several types of leukemia (9). Consequently, therapeutic and diagnostic strategies that target sialic acid and/or fucose residues may have broad applicability to a variety of cancers.

SUMMARY OF THE INVENTION

The invention provides methods and compositions for making and using functionalized glycoconjugates. For example, novel and/or unnatural sugars are incorporated into cell associated oligosaccharides using resident pathways of oligosaccharide biosynthesis to expand the informational repertoire of the plasma membrane.

Disclosed methods for making glycoconjugates include (a) contacting a cell with a first monosaccharide, and (b) incubating the cell under conditions whereby the cell (i) internalizes the first monosaccharide, (ii) biochemically processes the first monosaccharide into a second monosaccharide, (iii) conjugates the second monosaccharide to a carrier to form a glycoconjugate, and (iv) extracellularly expresses the glycoconjugate to form an extracellular glycoconjugate comprising a selectively reactive functional group. In a particular embodiments, the first monosaccharide comprises a chemically reactive functional group such as a ketone, which is incorporated into the second monosaccharide, the glycoconjugate and the extracellular glycoconjugate, the first functional group is N-linked in the first monosaccharide, and the first monosaccharide comprises ManLev.

The invention also includes methods for forming a wide variety of products at a cell. The products may provide a label, a binding site, a modulator of cell function such as a drug or toxin, a radiative emission, etc. These methods comprise the steps of making a glycoconjugate according to the invention and then contacting the functional group of the extracellularly expressed glycoconjugate with an agent which selectively reacts with the functional group to form a product. In a particular embodiment, the agent comprises a functional group moiety, such as a hydrazide, which selectively reacts with the functional group of the extracellular glycoconjugate to form a covalent bond, and an effector moiety, such as a drug, which modulates a function of a cell.

The subject compositions include cyto-compatible monosaccharides comprising a nitrogen or ether linked functional group, such as a ketone, selectively reactive at a cell surface and compositions and cells comprising such saccharides.

DESCRIPTION OF PARTICULAR EMBODIMENTS OF THE INVENTION

Figure 1:
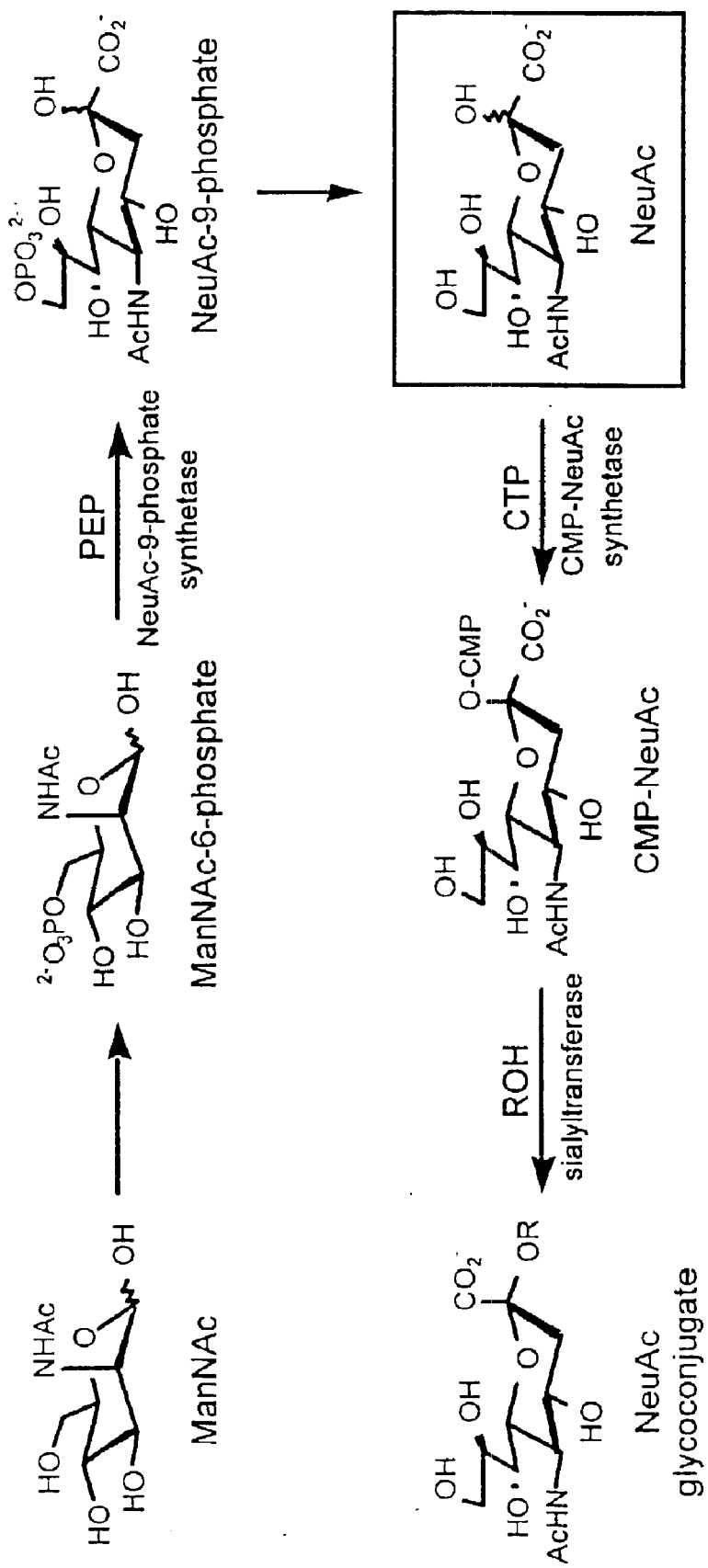
FIG. 1. The biosynthetic pathway for sialoglycoconjugates.

A particular disclosed method for making glycoconjugates involves: a) contacting a cell with a first monosaccharide comprising a first functional group, and b) incubating the cell under conditions whereby the cell (i) internalizes the first monosaccharide, (ii) biochemically processes the first monosaccharide into a second monosaccharide which comprises a second functional group, (iii) conjugates the second monosaccharide to a carrier to form a glycoconjugate comprising a third functional group, and (iv) extracellularly expresses the glycoconjugate to form an extracellular glycoconjugate comprising a fourth, selectively reactive, functional group.

The extracellular glycoconjugate may be presented in multiple forms such as membrane-associated, e.g. a membrane bound glycolipid or glycoprotein, associated with cell-proximate structures, e.g. extracellular matrix components or neighboring cells, or in a surrounding medium or fluid, e.g. as a secreted glycoprotein. The selective reactivity of the fourth functional group permits selective targeting of the glycoconjugate as presented by the cell. For example, fourth functional groups of surface associated glycoconjugates must provide a reactivity that permits the selective targeting of the glycoconjugate in the context of the associated region of the cell surface. Preferentially reactivity may be effected by a more reactive context, i.e. the glycoconjugate-associated fourth functional group provides greater accessibility, greater frequency or enhanced reactivity as compared with such functional groups present proximate to the site of, but not associated with the glycoconjugate; or, in a preferred embodiment, the fourth functional group is unique to the region of glycoconjugate presentation.

The selective reactivity provided by the fourth functional group may take a variety of forms including nuclear reactivity, such as the neutron reactivity of a boron atom, and chemical reactivity, including covalent and non-covalent binding reactivity. In any event, the fourth functional group should be sufficient for the requisite selective reactivity. A wide variety of chemical reactivities may be exploited to provide selectivity, depending on the context of presentation. For example, fourth functional groups applicable to cell surface-associated glycoconjugates include covalently reactive groups not normally accessible at the cell-surface, including alkenes, alkynes, dienes, thiols, phosphines and ketones. Suitable non-covalently reactive groups include haptens, such as biotin, and epitopes such as dinitrophenol.

In one embodiment of the invention, the nature of the expressed glycoconjugate is a function of the first monosaccharide, the cell type and incubation conditions. In this embodiment, the resident biochemical pathways of the cell act to biochemically process the first monosaccharide into the second monosaccharide, conjugate the second monosaccharide to an intracellular carrier, such as an oligo/polysaccharide, lipid or protein, and extracellularly express the final glycoconjugate. Alternatively, the expressed glycoconjugate may also be a function of further manipulation. For example, the fourth functional group may result from modifying the third functional group as initially expressed by the cell. For example, the third functional group may comprise a latent, masked or blocked group that requires a post-expression treatment, e.g. chemical cleavage or activation, in order to generate the fourth functional group. Such treatment may be effected by enzymes endogenous to the cell or by exogenous manipulation. Hence, the third and fourth functional groups may be the same or different, depending on cellular or extracellular processing events.

As indicated, a functional group can be a masked, latent, inchoate or nascent form of another functional group. Examples of masked or protected functional groups and their unmasked counterparts are provided in Table 1. Masking groups may be liberated in any convenient way; for example, ketal or enols ether may be converted to corresponding ketones by low pH facilitated hydrolysis. Alternatively, many specific enzymes are known to cleave specific protecting groups, thereby unmasking a functional group.

TABLE 1

Examples of masking functional groups and their unmasked counterparts

| Masking group | Unmasked group |
|---|---|
| dialkyl ketal | ketone |
| acetal | aldehyde |
| enol ether | ketone or aldehyde |
| oxime | ketone |
| hydrazone | ketone |
| thioester | thiol |
| cobalt-complexed alkyne | alkyne |

In contrast, the nature of the intracellular glycoconjugate (comprising the third functional group) is generally solely a function of the first monosaccharide, the cell type and incubation conditions, i.e. the first and second monosaccharides and the saccharide moiety incorporated into the intracellular glycoconjugate (as well as the first, second and third functional groups) may be the same or different depending on cellular processing events. For example, the first monosaccharide or functional group, cell and conditions may interact to form a chemically distinct second monosaccharide or functional group, respectively. For example, many biochemical pathways are known to interconvert monosaccharides and/or chemically transform various functional groups. Hence, predetermined interconversions are provided by a first monosaccharide, cell and incubation condition selection.

The first monosaccharide is selected to exploit permissive biochemical pathways of the cell to effect expression of the extracellular glycoconjugate. For example, many pathways of sialic acid biosynthesis are shown to be permissive to a wide variety of mannose and glucose derivatives. The first functional group may be incorporated into the first monosaccharide in a variety of ways. In preferred embodiments, the functional group is nitrogen or ether linked.

A wide variety of cells may be used in the disclosed methods including eukaryotic, especially mammalian cells and prokaryotic cells. The cells may be in culture, e.g. immortalized or primary cultures, or in situ, e.g. resident in the organism.

The invention also provides methods for forming products at a cell. Generally, these methods involve expressing an extracellular glycoconjugate as described above wherein the expressed glycoconjugate is retained proximate to the cell; for example, by being bound to membrane or extracellular matrix components. Then the fourth functional group is contacted with an agent which selectively reacts with the fourth functional group to form a product.

A wide variety of agents may be used to generate a wide variety of products. Generally, agent selection is dictated by the nature of the fourth functional group and the desired product. For example, with chemically reactive fourth functional groups, the agent provides a fifth functional group which selectively chemically reacts with the fourth functional group. For example, where the fourth functional group is a ketone, suitable fifth functional groups include hydrazines, hydroxylamines, acyl hydrazides, thiosemicarbazides and beta-aminothiols. In other embodiments, the fifth functional group is a selective noncovalent binding group, such as an antibody idiotope. In yet other embodiments, suitable agents include radioactivity such as alpha particles which selectively react with fourth functional groups comprising radiosensitizers such as boron atoms; oxidizers such as oxygen which react with fourth functional groups comprising a surface metal complex, e.g to produce cytotoxic oxidative species; etc. Alternatively, a functional group on the cell surface might have unique properties that do not require the addition of an external agent, e.g. a heavy metal which serves as a label for detection by electron microscopy. Further examples of products formed by the interaction of a cell surface functional group and an agent are given in Table 2.

TABLE 2

Examples of functional groups, agents and their products

| Functional group | Agent | Product |
| --- | --- | --- |
| ketone | hydrazide | hydrazone |
| diene | dienophile | Diels-Alder adduct |
| thiol | alpha-bromo amide | thioether |
| boron | neutrons | radiation |
| biotin | avidin | biotin-avidin complex |

TABLE 2-continued

Examples of functional groups, agents and their products

| Functional group | Agent | Product |
| --- | --- | --- |
| dinitrophenol (DNP) | anti-DNP antibodies | DNP-antibody complex |
| Fluorescein | UV light | green light |
| iron complex | oxygen | peroxy radicals |

Frequently, the agent comprises an activator moiety which provides a desired activity at the cell. A wide variety of activator moieties may be used, including moieties which alter the physiology of the cell or surrounding cells, label the cell, sensitize the cell to environmental stimuli, alter the susceptibility of the cell to pathogens or genetic transfection, etc. Exemplary activator moieties include toxins, drugs, detectable labels, genetic vectors, molecular receptors, and chelators.

Figure 11:
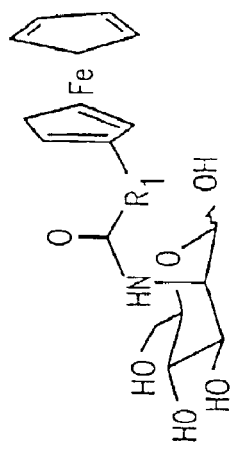
FIG. 11. Examples of functional-group bearing mannosamine derivatives.
Figure 11:
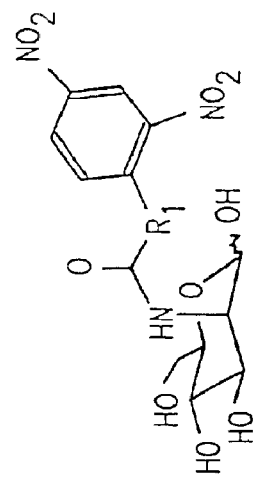
Figure 11:
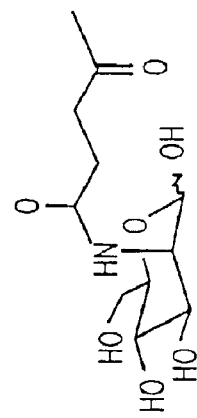
Figure 11:
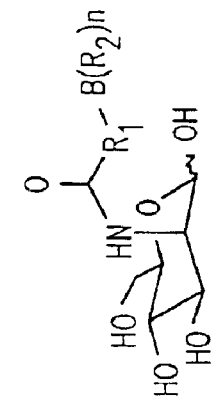
Figure 11:
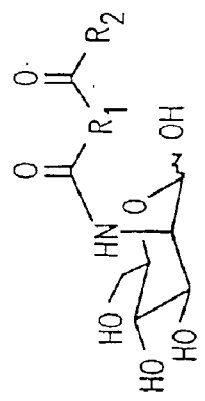
Figure 11:
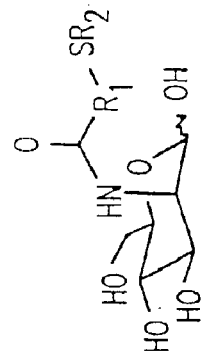
Figure 12:
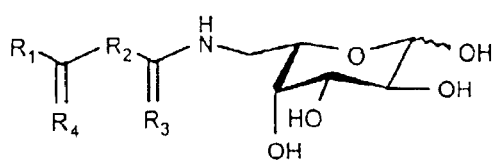
FIG. 12. Examples of functional-group bearing fucose derivatives.
Figure 12:
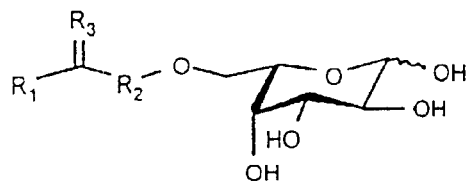
Figure 12:
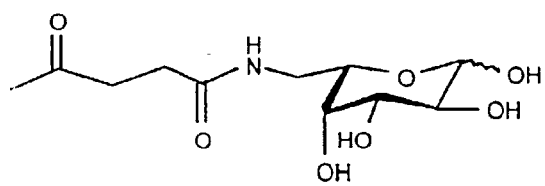
Figure 12:
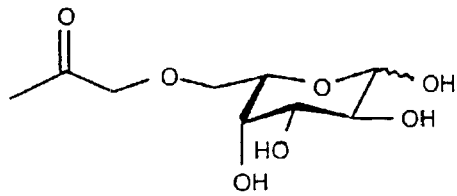
Figure 12:
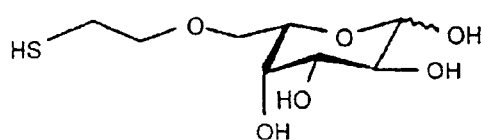
Figure 12:
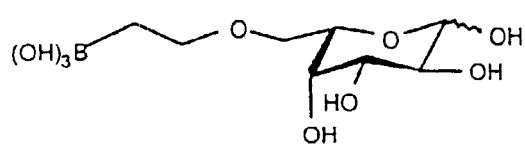

The invention provides a wide variety of compositions useful in the disclosed methods, including compositions comprising cyto-compatible monosaccharides comprising a functional group, preferably a nitrogen or ether linked functional group, which group is selectively reactive at a cell surface. Exemplary functional groups of such compounds include alkynes, dienes, thiols, phosphines, boron and, especially, ketones. Exemplary mannose and fucose derivatives are shown in FIGS. 11 and 12, respectively. The term substituted or unsubstituted alkyl is intended to encompass alkoxy, cycloalkyl, heteroalkyl, etc. Similarly, the term substituted or unsubstituted aryl is intended to encompass aryloxy, arylalkyl (including arylalkoxy, etc.), heteroaryl, arylalkynyl, etc.; the term substituted or unsubstituted alkenyl is intended to analogously encompass cycloalkenyl, heteroalkenyl, etc.; etc. Analogous derivatives are made with other monosaccharides having permissive pathways of bioincorporation. Such monosaccharides are readily identified in convenient cell and protein-based screens, such as described below. For example, functionalized monosaccharides incorporated into cell surface glycoconjugates can be detected using fluorescent labels bearing a complementary reactive functional group (i.e., agent). A cell-based assay suitable for mechanized high-throughput optical readings involves detecting ketone-bearing monosaccharides on cell surfaces by reaction with biotin hydrazide, followed by incubation with FITC-labeled avidin and the quantitating the presence of the fluorescent marker on the cell surface by automated flow cytometry. A convenient protein-based screen involves isolating the glycocojugate, e.g. gel blots, affinity immobilization, etc, and detecting with the complementary reactive probe, e.g. detone-bearing glycoconjugates detected with biotin hydrazide, followed by incubation with avidin-alkaline phosphatase or avidin-horseradish peroxidase. Alternatively, monosaccharides bearing unusual functional groups can also be detected by hydrolysis of the glycoconjugate followed by automated HPLC analysis of the monosaccharides.

For use in methods applied to cells in situ, the compositions frequently further comprise a physiologically acceptable excipient and/or other pharmaceutically active agent to form pharmaceutically acceptable compositions. Hence, the invention provides administratively convenient formulations of the compositions including dosage units which may be incorporated into a variety of containers. For in situ administration, the compositions are provided in any convenient way, such as oral, parenteral or topical routes. Generally the compounds are administered in dosages ranging from about 2 mg to up to about 2,000 mg per day, although variations will necessarily occur depending on the method application or target, the host and the route of administration. Preferred dosages are administered orally in the range of about 0.05 mg/kg to about 20 mg/kg, more preferably in the range of about 0.05 mg/kg to about 2 mg/kg, most preferably 0.05 to about 0.2 mg/kg of body weight per day.

EXPERIMENTAL PROCEDURES

The biosynthesis of N-acetylneuraminic acid (NeuAc, the most abundant member of the sialic acid family) glycoconjugates is shown in FIG. 1. N-Acetylmannosamine (ManNAc) is phosphorylated and then condensed with phosphoenol pyruvate (PEP) to form NeuAc-9-phosphate in a reaction catalyzed by the enzyme NeuAc-9-phosphate synthetase (10). After dephosphorylation, NeuAc is converted to CMP-NeuAc by CMP-sialic acid synthetase. CMP-NeuAc is transported into the appropriate cellular compartments, and the NeuAc residue is transferred by a sialyltransferase onto the terminus of oligosaccharides attached to proteins or lipids.

We hypothesized that such saccharide biochemical pathways of the cell might be appropriated for the presentation of unique functional groups on cell surfaces. First, experiments have been reported suggesting that individual, isolated enzymes of the sialic acid biosynthetic pathway may be permissive for substrate variants in vitro (11–15). Furthermore, conservative changes within a natural functional group (the N-acetyl group of ManNAc extended to N-propanoyl, N-butanoyl or N-pentanoyl) may be also be permitted by the same pathway in cell culture and in vivo (16,17). While our hypothesized permissive introduction of entirely new functional groups was without precedent—the biosynthetic machinery for the other major biopolymers (i.e., proteins and nucleic acids) is quite restrictive—we anticipated that, if possible, such oligosaccharides would prove remarkably versatile hosts for biosynthetic labels, effectors and probes in vivo.

We initially chose the ketone for cell surface display based on two considerations. First, the ketone is chemically unique to the cell surface since none of the naturally occurring amino acids, glycoconjugates or lipids possess a ketone group. Second, the ketone can be chemoselectively ligated with hydrazides to form the corresponding acyl hydrazones under physiological conditions, and shows no appreciable reactivity with the functional groups found in biomolecules. These properties of the ketone group have been widely exploited for the chemoselective ligation of proteins and small molecules (18,19). Furthermore, hydrazone formation between small molecule drugs has been accomplished in whole animals and human subjects, setting the precedent for the application of our cell surface targeting approach to anti-cancer therapy (20). Although ketones and hydrazides react readily at normal physiological pH (pH= 7.3–7.6), the reaction rate is enhanced up to 10-fold at lower pHs (pH=5). Because the extracellular pH in many tumors is slightly lower (ranging as low as 5.6) than in normal tissue (21), hydrazide-conjugated agents have an additional level of selectivity for tumor environments over normal tissue.

Figure 2:
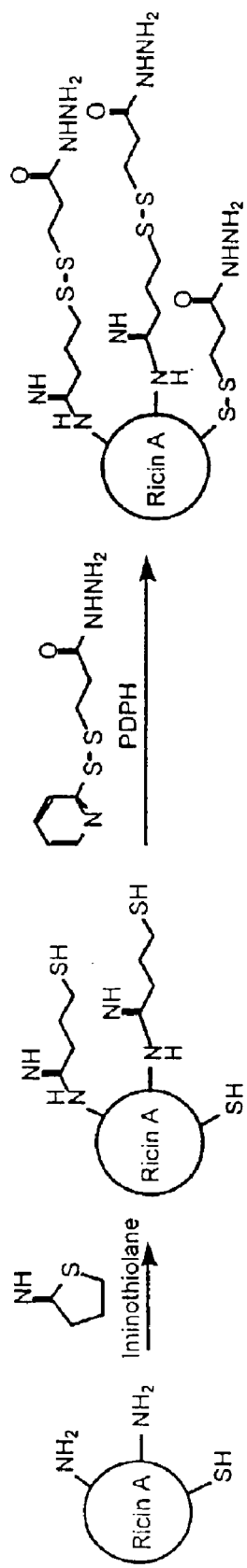
FIG. 2. Synthesis of a ricin-hydrazide conjugate.
Figure 3:
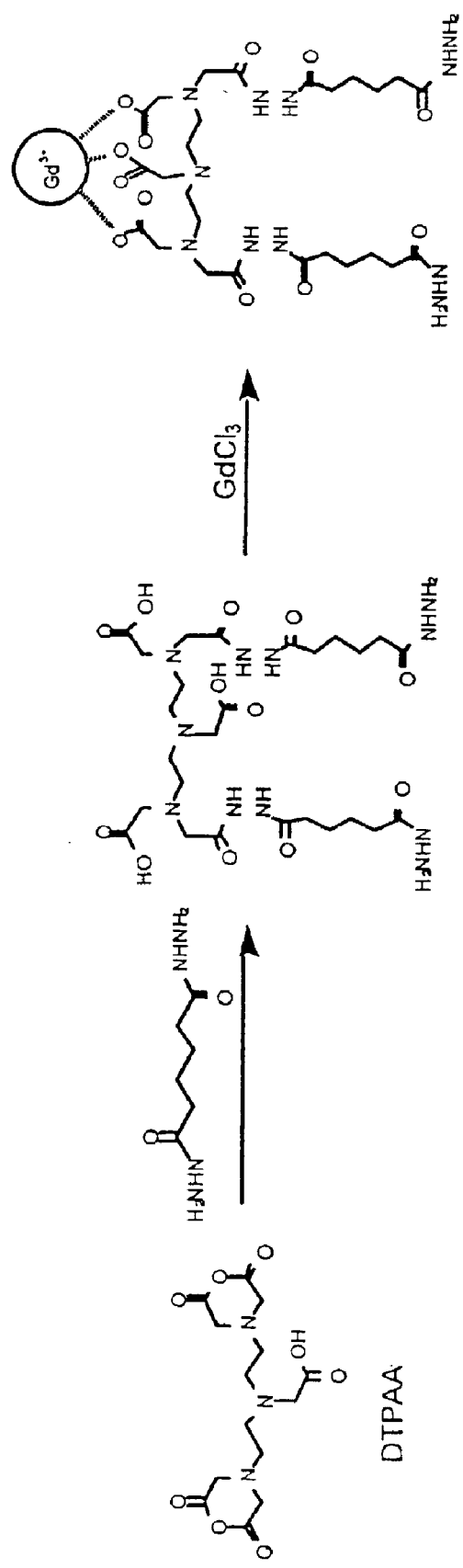
FIG. 3. Synthesis of a bis(hydrazide) $Gd^{3+}$ chelator for ketone-directed MRI.

The prevalence of sialic acid on cancer-associated glycoproteins and glycolipids makes this residue an ideal vehicle for the presentation of ketone groups capable of directing hydrazide-conjugated toxins or probes to cancer cells. We initially demonstrated the feasibility of this approach with the plant-derived toxin ricin, which has been widely explored for use in cancer therapy. Ricin is composed of two chains, A and B, linked together by a disulfide bond. The B chain binds to cell-surface galactose residues, thereby delivering the toxic A chain to the cell surface which is followed by internalization via constitutive endocytotic processes. As demonstrated in the Examples below, we constructed a modified ricin derivative in which hydrazide groups are attached to the surface of the A chain via disulfide linkers, replacing the B chain altogether and providing a targeting mechanism to ketone-coated cells (FIG. 2). Ricin A chain was treated with iminothiolane to convert two surface-accessible lysine residues to the corresponding thiol derivatives, affording a total of three accessible thiols for further conjugation. Further reaction with PDPH installed the desired hydrazide groups.

The toxicity of ricin-hydrazide is readily evaluated with a variety of transformed cell types in the presence and absence of ketone expression. For example, with Jurkat lymphoma, the concentrations of ricin-hydrazide required for 50% cell death ($LD_{50}$) is evaluated by treatment of cell cultures with the toxin for 2 hours, followed by removal of the toxin from the suspension and incubation of the cells for an additional 24 h. Live cells are counted using a standard haemocytometer-based assay and comparisons made between ketone-coated and unmodified cells, using native ricin A chain as a control for background toxicity. With the optimal parameters established, a panel of transformed cell types are compared with their non-transformed counterparts with respect to ketone incorporation and $LD_{50}$ of ricin-hydrazide. In addition, our drug delivery efforts are extended to other toxins requiring a cell-surface target for optimal activity, e.g. abrin toxin and diptheria toxin, and hydrazide-ketone ligation is used to deliver small molecule drugs to cells via a cleavable disulfide linker.

The availability of cancer-specific magnetic resonance imaging (MRI) contrast reagents has revolutionized our ability to diagnose lesions at their earliest stages. The most commonly used contrast reagents are based on $Gd^{3+}$ in the form of a protein conjugate (3). We have designed a hydrazide-conjugated $Gd^{3+}$ reagent (FIG. 3) capable of imaging ketone-expressing cells selectively. The synthesis of this complex involves the reaction of the commercially available DTPAA with adipic acid dihydrazide to form the bis-hydrazide product which chelates $Gd^{3+}$ in an essentially irreversible manner. This derivative reacts specifically with ketones expressed on highly sialylated tumor cells. Again, since the hydrazone formation reaction is accelerated in acidic environments, further selectivity for tumor cells is achieved.

Initial demonstrations are conducted on cultured lymphoma cells that heave been treated with ManLev to induce ketone expression. We use $Eu^{3+}$ as a $Gd^{3+}$ mimic for initial experiments since $Eu^{3+}$ is highly fluorescent (emission max=590 nm) and is therefore amenable to flow cytometry analysis. The cells are stained with the bis-hydrazide chelator loaded with $Eu^{3+}$ cations, then washed and analyzed by flow cytometry. The optimal parameters (i.e., concentration of chelator and time of incubation) for selective cell-surface staining are determined, particularly, the staining levels of mixed populations of normal and cancerous lymphocytes after parallel treatment with ManLev. In a two color flow cytometry experiment, we correlate $Eu^{3+}$ staining with the level of staining of specific tumor or normal cell markers, showing that cancerous lymphocytes are stained at significantly higher levels that their normal counterparts. This correlation demonstrates the relative specificity of our hydrazide-based contrast reagent.

With the optimal staining parameters established in vitro, we demonstrate ManLev uptake and $Gd^{3+}$ staining in mice and in rabbits. Mice (balb/c) are injected IV with various doses of ManLev in 8 boluses over a 2-day period using a protocol for the uptake and cellular incorporation of mannosamine derivatives (22). The mice are then be injected with the $Gd^{3+}$-loaded bis(hydrazide) chelator and after a 6 hour period the mice are anesthetized and subjected to whole animal MRI.

To determine the selectivity of ManLev uptake and metabolism in mice carrying surgically implanted tumors, the $Gd^{3+}$-loaded bis(hydrazide) chelator is used as a marker for ketone presentation in vivo, and correlations made among tumor type and staining intensity. Organs that stain at high levels are identified and membrane glycoproteins from these tissues isolated and biochemically characterized to confirm the presence of high levels of ketone-modified sialic acids. In addition, the staining levels of normal organs are compared to the corresponding cancerous tissue to evaluate the selectivity of $Gd^{3+}$ localization.

Figure 4:
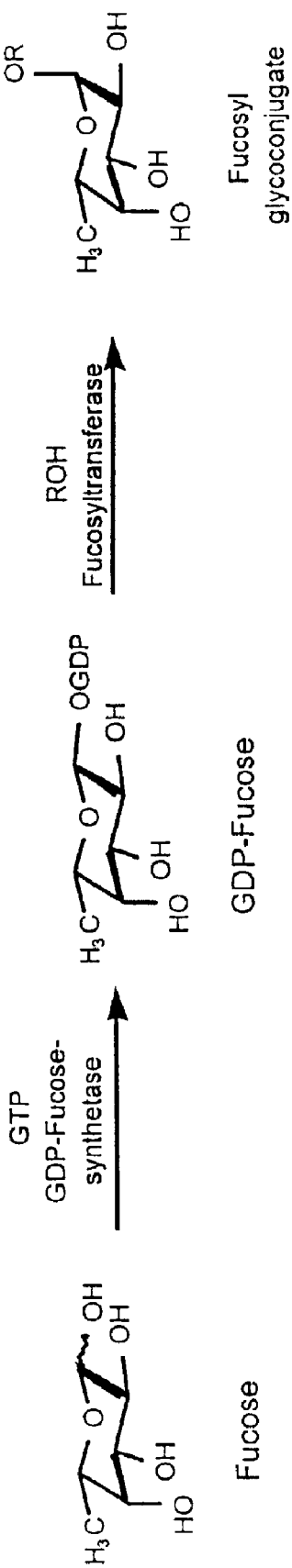
FIG. 4. Biosynthetic pathway for cell surface fucosides.

In addition to high levels of sialic acid, many cancer cells express elevated levels of cell surface fucose residues. There are two pathways for the biosynthesis of fucosides: one begins with mannose and the other with free fucose. The latter pathway is advantageous in that since it involves fewer transformations and, therefore, fewer potential biosynthetic bottlenecks. Fucose is taken up from the extracellular milieu and converted to the activated form, GDP-fucose, by a GDP-fucose synthetase (FIG. 4). The fucose residue is then transferred onto the terminus of an oligosaccharide chain by a fucosyltransferase within the Golgi compartment. A recent in vitro study reported that a human fucosyltransferase may be permissive for substituents attached at C-6, which is a simple methyl group in the native sugar (23). Hence, w hypothesized that the C-6 position might also be a promising site for derivitization of fucose with a ketone functionality.

Figure 5:
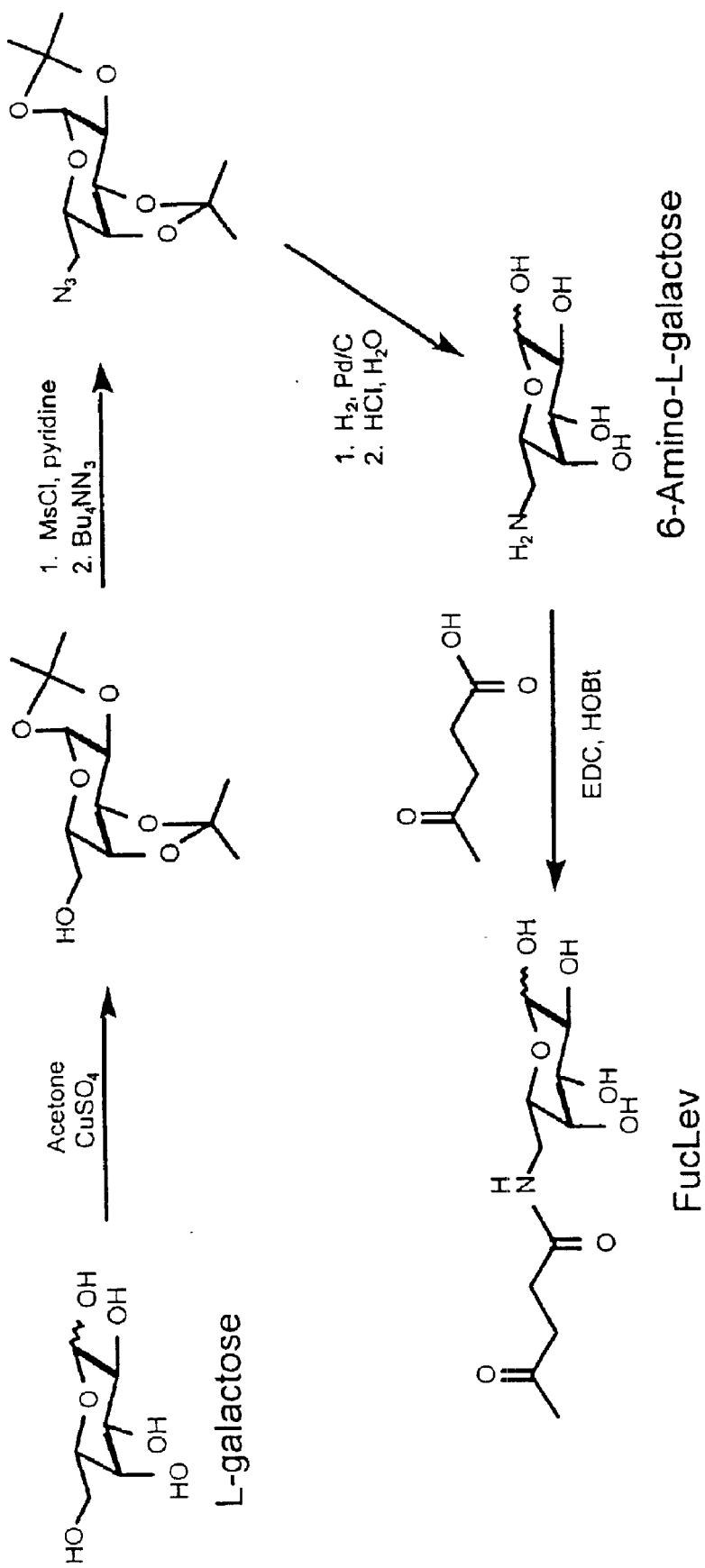
FIG. 5. Synthesis of FucLev, an unnatural ketone-modified fucose derivative.

6-N-levulinamido fucose (FucLev), which possesses a ketone groups, from L-galactose is synthesized as shown in FIG. 5. L-Galactose is protected as the 1,2-3,4-di-O-ispropylidene derivative. The 6-OH is converted first to the mesylate and then to the corresponding azide. Reduction followed by deprotection affords 6-amino fucose. Finally, acylation with levulinic acid provides the desired ketone-modified fucose derivative. The uptake and metabolism of this compound is evaluated in Jurkat lymphomas and HL60 cells (a human neutrophil cell line), both of which express high levels of fucose on cell surface glycoconjugates. The expression of ketones is assayed with biotin hydrazide followed by flow cytometry analysis as described for sialic acid-associated ketones, and the same targeting strategies using ricin-hydrazide and the $Gd^{3+}$-loaded bisthydrazide) chelator are applied.

Synergistic tumor cell targeting is effected by incorporating two orthogonal unnatural functional groups into sialic acid and fucose residues in the same cancer cell. Cells with high levels of both sialic acid and fucose are more susceptible to agents capable of binding both functional groups.

The following examples are offered by way of illustration and not by way of limitation.

EXAMPLES

Figure 6:
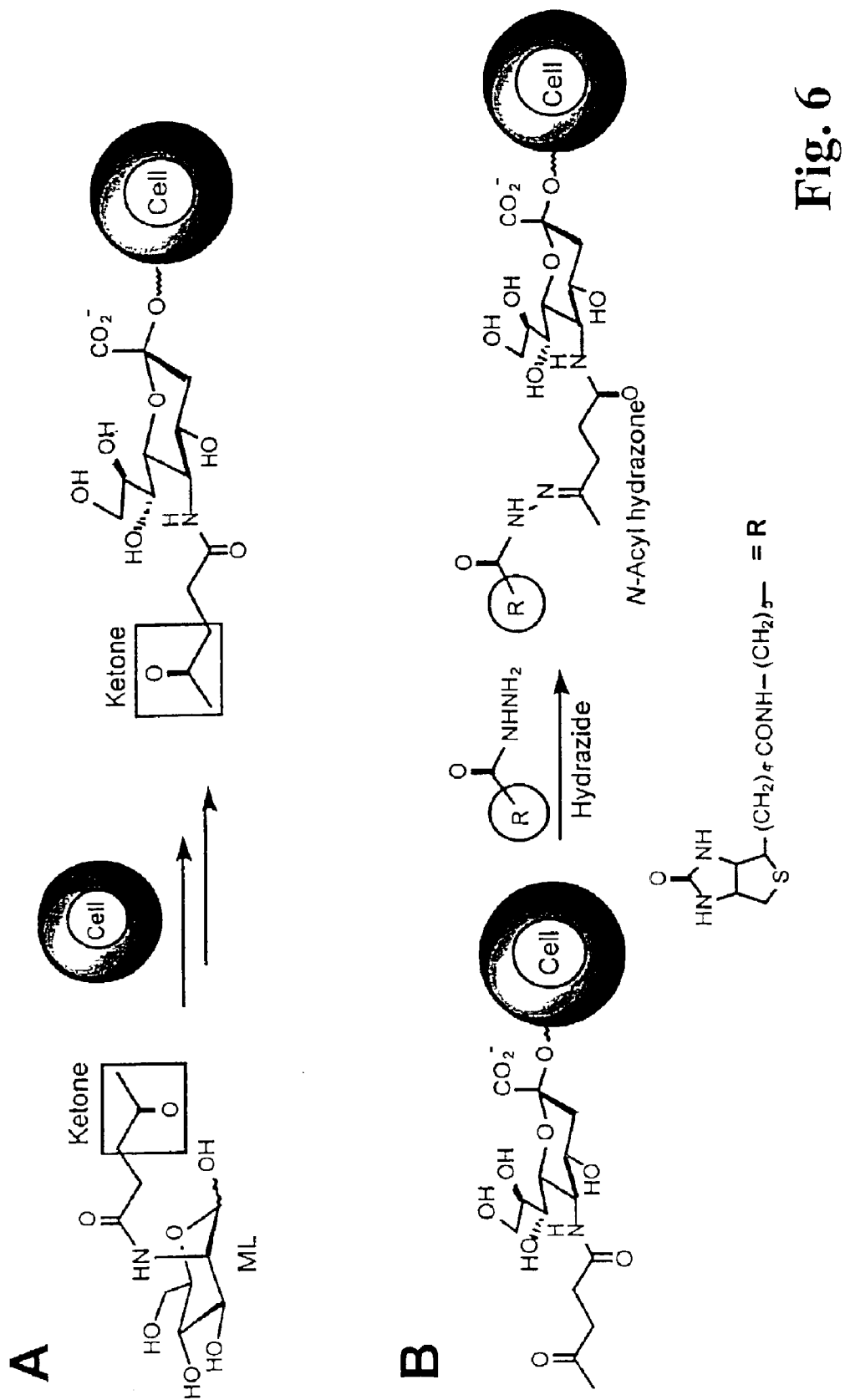
FIG. 6. Biosynthetic incorporation of ketone groups into cell-surface associated sialic acid. (A) N-Levulinoyl mannosamine (ManLev) is metabolically converted to the corresponding cell surface sialoside. (B) Cells displaying ketone groups can be chemoselectively ligated to hydrazides under physiological conditions through the formation of an acyl hydrazone.
Figure 7:
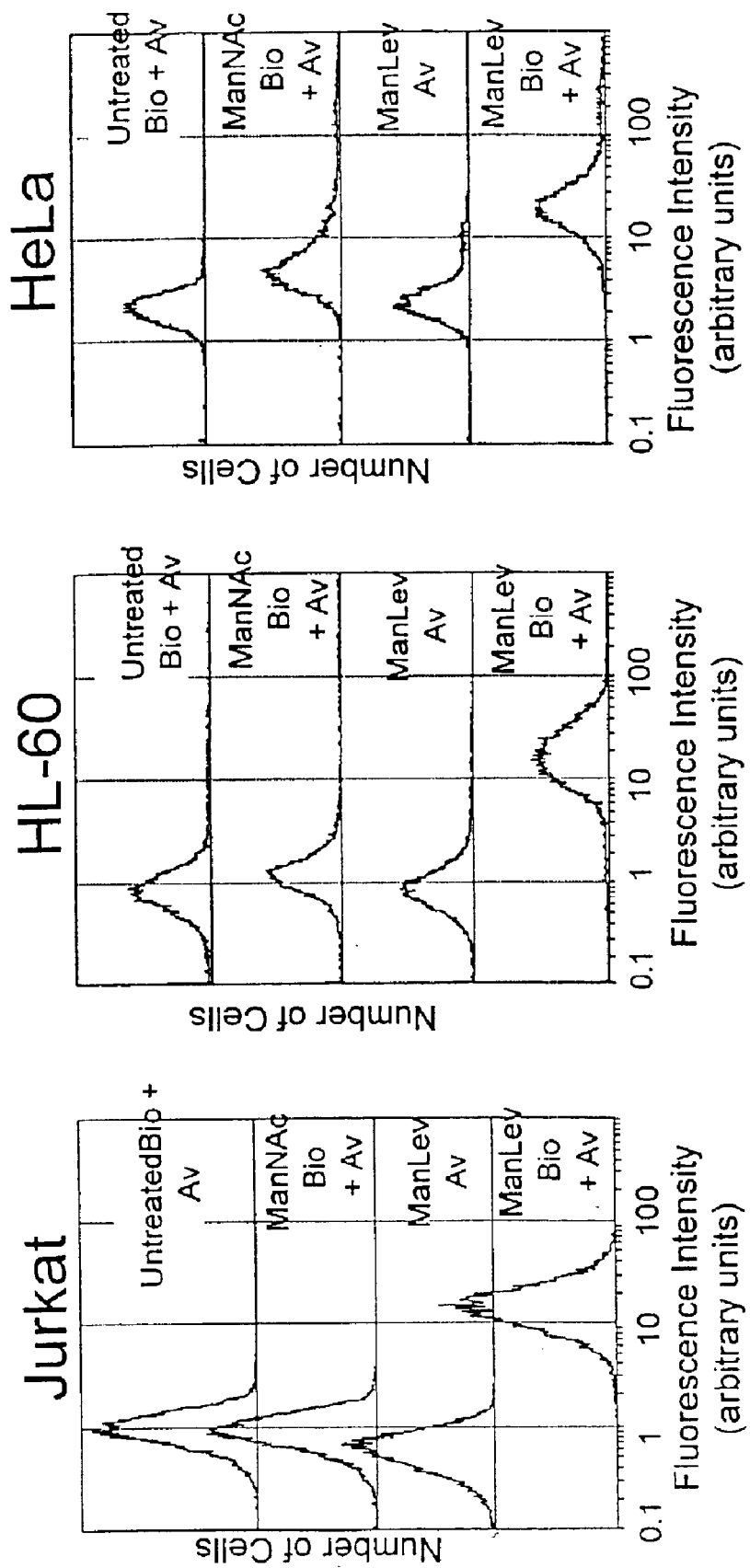
FIG. 7. Ketone expression in Jurkat, HL-60, and HeLa cells. Cells treated with buffer alone or with ManNAc showed only a background level of fluorescence. Cells treated with ManLev showed up to a 30-fold increase in fluorescence above the background level, which was dependent on both biotinamidocaproyl hydrazide (Bio) and FITC-avidin (Av) treatment. Similar results were obtained in three replicate experiments for each cell line.

We synthesized N-levulinoyl mannosamine (ManLev) (FIG. 6, A), which has the ketone functionality at the position normally occupied by the N-acetyl group in the natural substrate ManNAc. We selected three human cell lines, Jurkat (T cell-derived), HL-60 (neutrophil-derived) and HeLa (cervical epithelial carcinoma), to test the biosynthetic conversion of ManLev to the corresponding cell-surface associated, unnatural sialic acid (FIG. 6, A). Cells were treated with ManLev and the presence of ketone groups on the cell surface was determined by the chemoselective ligation of a hydrazide-based probe, biotinamidocaproyl hydrazide (FIG. 6, B). Note that in this example, cell surface ketones were conjugated to biotinamidocaproyl hydrazide to provide a tag for subsequent detection with FITC-avidin; however, any hydrazide-derivatized molecule can be used selectively remodel the surface of ketone-expressing cells. The cells were analyzed by flow cytometry after staining with FITC-avidin (24). The Jurkat, HL-60, and HeLa cells treated with ManLev showed a large increase in fluorescence intensity compared to cells treated with buffer or the natural derivative ManNAc (FIG. 7). ManLev-treated cells that were stained with FITC-avidin alone, without prior biotinamidocaproyl hydrazide treatment, showed only a background level of fluorescence. These results indicate that ManLev-treated cells express cell surface-associated ketone groups and can be chemoselectively decorated with hydrazide conjugates, even in the presence of serum.

We performed a series of experiments to demonstrate that the ketone groups are displayed on the cell surface in the form of modified sialoglycoconjugates. Jurkat cells were treated with tunicamycin, an inhibitor of N-linked protein glycosylation, prior to incubation with ManLev (25,26). We anticipated a dramatic reduction in ketone expression on the basis of the observation that most mature (and therefore sialylated) oligosaccharides on Jurkat cells are found on N-linked rather than O-linked glycoproteins (27). Indeed, ketone expression resulting from ManLev treatment was inhibited by tunicamycin in a dose-dependent fashion (FIG. 8, A), indicating that the ketone groups are presented on oligosaccharides and are not nonspecifically associated with cell-surface components. In contrast, ketone expression in HL-60 and HeLa cells was unaffected by tunicamycin, but was instead blocked by α-benzyl N-acetylgalactosamnine, an inhibitor of O-linked glycosylation, consistent with the high expression of mucin-like molecules on myeloid- and epithelial-derived cell lines.

Although we predicted that ManLev would be converted into the corresponding sialoside, we addressed the possibility that ketone expression resulted from conversion of ManLev to N-levulinoyl glucosamine (GlcLev) by the enzyme that interconverts ManNAc and GlcNAc. In that GlcNAc is incorporated into most glycoproteins, GlcLev would have many avenues for cell surface expression. Synthetic GlcLev was incubated with Jurkat cells, and flow cytometry analysis revealed only background fluorescence, indicating that unnatural sialosides are the major biosynthetic products of ManLev.

Since the commercially available sialidases were found to be inactive against N-levulinoyl sialosides, in accordance with their known reduced activity against sialosides with other unnatural N-acyl groups (28), abrogating the fluorescence signal by treatment with sialidase enzymes to show cell-surface expression of ketone-bearing sialic acids was not practical. We therefore evaluated the effects of ManLev treatment on the amount of normal sialic acid on Jurkat cells, expecting a reduction. Indeed, the amount of sialic acid released from ManLev-treated cells by sialidase digestion, as quantified by high-pH anion exchange chromatography (HPAEC), was found to be approximately 10-fold lower than that released from ManNAc-treated cells (29).

Two possible explanations for the observed reduction in normal sialic acid on ManLev-treated cells are (i) normal sialic acid is replaced with the unnatural sialic acid during incubation with ManLev, or (ii) the biosynthesis of all sialosides is suppressed during incubation with ManLev. Inhibition of sialoside biosynthesis would cause an increase in exposed terminal galactose residues, the penultimate residue in the majority of sialoglycoconjugates. We therefore examined the effect of ManLev treatment on the binding of the galactose-specific lectin ricin to Jurkat cells (30). Ricin binding to ManLev-treated and untreated cells was found to be identical (FIG. 8, B), indicating that ManLev-treatment does not inhibit sialoside biosynthesis. Sialidase treatment of normal Jurkat cells increased ricin binding over background levels as expected (31). When ManLev-treated cells were digested with sialidase, however, a much smaller increase in ricin binding was observed. This finding indicates the substitution of normal sialic acids with unnatural sialic acids refractory to enzymatic cleavage in ManLev-treated cells.

Figure 8:
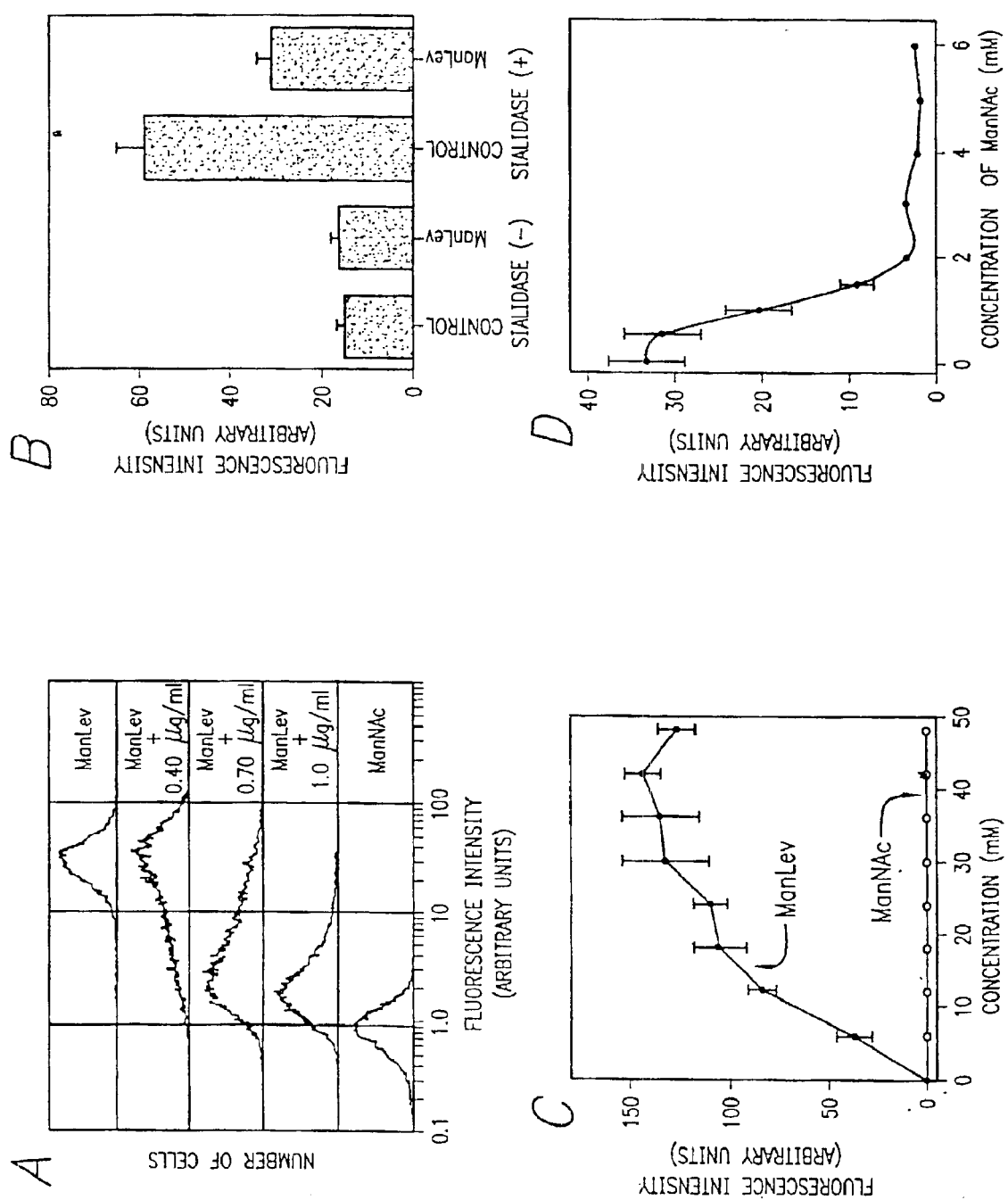
FIG. 8. Ketone groups are expressed within cell-surface sialic acids. (A) Tunicamycin inhibits ketone incorporation in a dose-dependent fashion, confirming the presence of ketones on N-linked oligosaccharides (26). Identical results were obtained in three replicate experiments. (B) Ricin binding of normal and ManLev-treated Jurkat cells with and without sialidase treatment. Ricin binding was quantified by staining with FITC-RCA$_{120}$ (Sigma) followed by analysis by flow cytometry (24). Error bars represent the standard deviation of the mean for three replicate experiments. (C) Ketone incorporation into cell-surface sialosides is dose dependent and saturable. Jurkat cells were incubated with increasing concentrations of ManNAc for 48 h, stained with Bio and Av and analyzed by flow cytometry. Data from four experiments is shown. (D) ManNAc competes with ManLev and inhibits ketone incorporation. Jurkat cells were incubated with ManLev (5 mM) and increasing concentrations of ManNAc for 48 h, and ketone expression was quantified by flow cytometry. Each data point represents the average from three experiments and error bars represent the standard deviation of the mean.

We have also determined the quantitative and physiological limits to the cell surface expression of reactive functional groups. Ketone expression is dose dependent and saturable in ManLev-treated Jurkat cells (FIG. 8, C). At saturation, we calculated the number of ketones accessible to chemoselective ligation and flow cytometry analysis to be approximately $1.8 \times 10^6$ per cell (32). No effects on cell morphology or the rate of cell growth were observed during prolonged (up to 6 weeks) treatment with ManLev. We therefore conclude that even at maximal levels, the presence of sialic acid-associated ketones does not grossly alter normal cellular functions. Additionally, we demonstrated that ketone expression was inhibited by the addition of ManNAc to ManLev-treated cells, confirming that both substrates compete in the same biosynthetic pathway (FIG. 8, D).

Our ability to manipulate the chemical reactivity of cell surfaces using biosynthetic processes opens the door to a myriad of applications. For example, cell surfaces can be engineered to present unique epitopes for the selective targeting of drugs, radionucleotides or imaging reagents, an alternative to well known immunotargeting strategies. Sialic acid residues are overexpressed on a number of human cancers (33), offering the expression of unnatural, reactive sialic acids as a possible mechanism to differentiate cancer cells from normal cells in a new targeting strategy.

Figure 9:
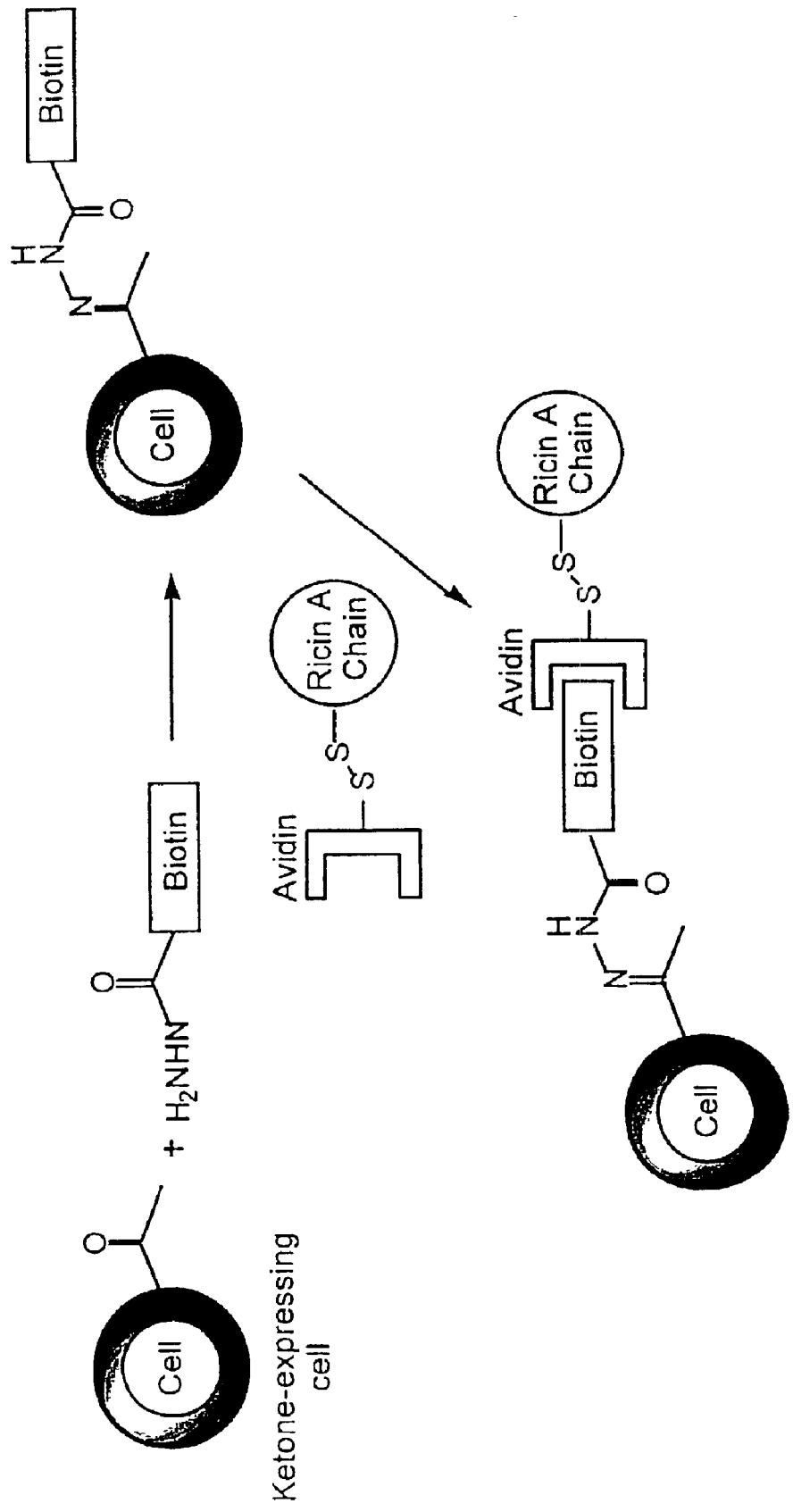
FIG. 9. A method for engineering unique cell-surface epitopes for selective drug-delivery: cells are treated with ManLev resulting in the expression of cell surface ketones. Reaction with biotin hydrazide results in the display of a unique molecular target on the cell surface, and a ricin A chain-avidin conjugate selectively targets biotin-modified cells, with varying concentrations of ManLev.
Figure 10:
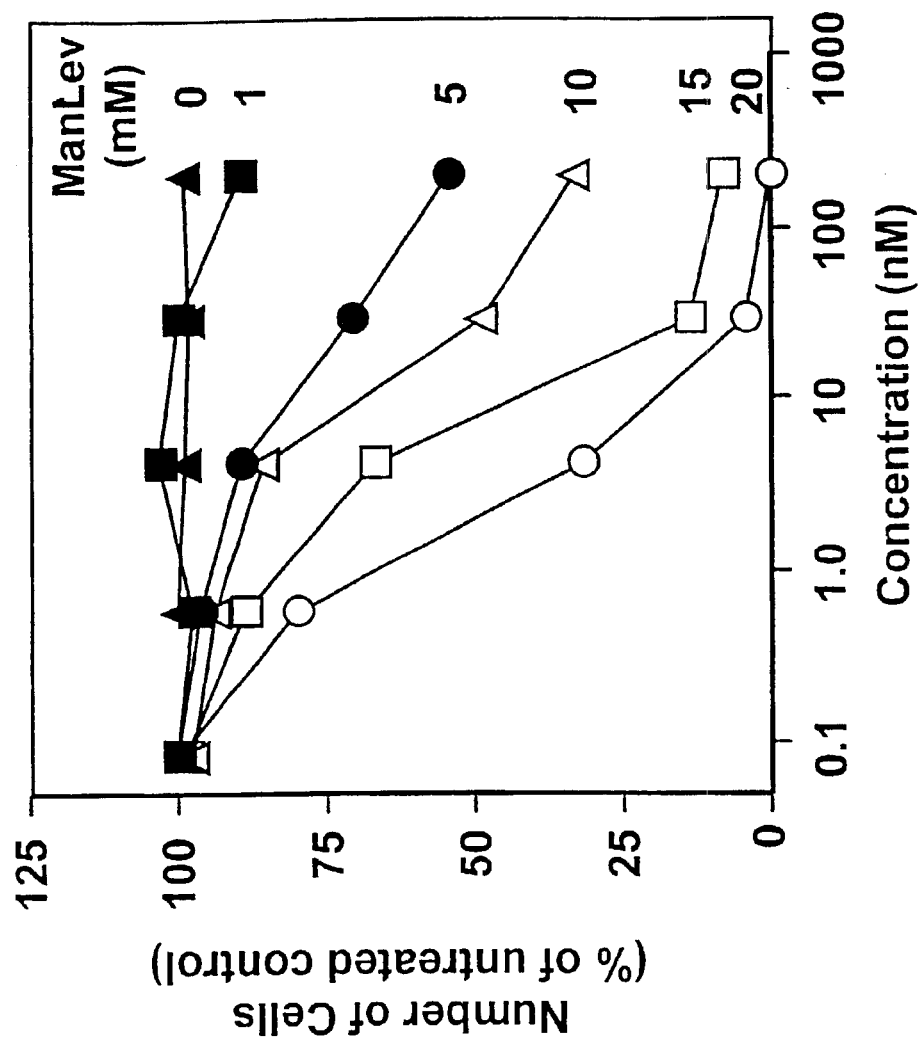
FIG. 10. A method for engineering unique cell-surface epitopes for selective drug-delivery: toxicity of the RTA-avidin conjugate against Jurkat cells treated with varying concentrations of ManLev.

We have demonstrated the viability of this approach by decorating cancer cell surfaces with biotin hydrazide, providing a unique cell surface epitope for the delivery of avidin-conjugated toxins (FIG. 9, A). We chose the ricin toxin A chain (RTA), a potent inhibitor of protein synthesis, as a model toxin on the basis of precedents in the field of immunotoxin research (34,35) and, accordingly, we prepared a disulfide-linked RTA-avidin conjugate using previously described methods (36,37). The disulfide linkage is commonly used in the preparation of immunoconjugates since it provides a mechanism for toxin release once the cell surface-bound conjugate enters the reducing environment of the cell's interior (38,39).

The selective toxicity of the RTA-avidin conjugate was evaluated using Jurkat cells treated with varying concentrations of ManLev and then decorated with the targeting epitope, biotin hydrazide (FIG. 9, B; 40). The toxicity of the conjugate was found to be dependent on the level of ketone expression: cells expressing high levels of ketones (>700,000 ketones/cell as estimated by flow cytometry analysis) were sensitive to the conjugate with $LD_{50}$'s in the 1–10 nM range. In contrast, the conjugate showed no toxicity against cells expressing low numbers of ketones (<50,000 ketones/cell). These results indicate that cell surfaces can be metabolically engineered to support selective drug delivery, and that the sensitivity of target cells can be controlled by modulating the expression level of the unique targeting epitope.

Other variations of this strategy are provided, such as the direct targeting of cell surface ketones with hydrazide-conjugated drugs or probes and the use of other mutually reactive organic functional group pairs. It should be noted that the chemoselective formation of hydrazone linkages among small molecule drugs has been accomplished in whole animals and human subjects. Other applications of cell surface remodeling include engineering new determinants for immunological recognition, tissue-specific cell trafficking, and cell adhesion to synthetic substrates.

PARENTHETICAL REFERENCES

1. Scientific American September, 1996.
2. J. M. Lord, L. M. Roberts, J. D. Robertus, *FASEB J.* 8, 201 (1994).
3. K. P. Aicher, et al., *Cancer Res.* 50, 7376 (1990).
4. (a) S. Sell, *Human Path.* 21, 1003 (1990). (b) W. J. Snell, et al., *Cell* 85, 629-(1996).
5. T. H. Brummendorf, et al., *Cancer Res.* 54, 4162 (1994).
6. N. S. Courtenay-Luck, et al. *Cancer Res.* 46, 6489 (1986).
7. J. R. Couto, et al., *Cancer Res.* 55, 5973s (1995).
8. R. Chignola, et al., *Int. J. Cancer* 61, 535 (1995).
9. T. Dohi, et al., *Cancer* 73, 1552 (1994).
10. L. Warren, *Bound carbohydrates in nature* (Cambridge Univ. Press, New York, 1994).
11. R. E. Kosa, et al., *Biochem. Biophys. Res. Commun.* 190, 914 (1993).
12. W. Fitz, C. -H. Wong, *J. Org. Chem.* 59, 8279 (1994).
13. S. L. Shames, et al., *Glycobiology* 1, 187 (1991).
14. M. A. Sparks, et al., *Tetrahedron* 49, 1 (1993).
15. C. -H. Lin, et al., *J. Am. Chem. Soc.* 114, 10136 (1992).
16. H. Kayser, et al., *J. Biol. Chem.* 267, 16934 (1992).
17. O. T. Keppler, et al., *J. Biol. Chem.* 270, 1308 (1995).
18. K. Rose, *J. Am. Chem. Soc.* 116, 30 (1994).
19. H. F. Gaertner, et al., *Bioconjugate Chem.* 3, 262 (1992).
20. D. Rideout, et al., *Biopolymers* 29, 247 (1990).
21. J. R. Griffiths *Br. J. Cancer* 64, 425 (1991).
22. H. Kayser, C. Ats, J. Lehmann, W. Reutter, *Experientia* 49, 885 (1993).
23. G. Srivastava, et al., *J. Biol. Chem.* 267, 22356 (1992).
24. Cultures of $2 \times 10^6$ cells were grown in media (DME) containing ManLev (5 mM), ManNAc or no sugar for 48 hours. Cells were then washed twice with biotin staining buffer (0.1% newborn calf serum (NCS) in phosphate buffered saline (PBS) pH=6.5) and resuspended at a density of $10^7$ cells/mL. Aliquots of $2 \times 10^6$ cells were suspended in 1.4 mL of biotin staining buffer and 400 µL of biotinamidocaproyl hydrazide (5 mM solution in PBS) or 400 µL of buffer. After 2 hours at rt, the cells were pelleted and washed twice with ice cold avidin staining buffer (0.1% $NaN_3$, 0.1% NCS in PBS pH=7.4). The cells were then suspended in 100 µL of FITC-avidin staining solution (5.6 µg/mL of FITC-avidin in avidin staining buffer). After a 10 minute incubation in the dark at 0° C., the cells were diluted with 2 mL of cold avidin staining buffer and washed twice. The cells were resuspended in 400 µL of avidin staining buffer and subjected to flow cytometry analysis.
25. F. M. Ausubel, Ed., *Inhibition of N-Linked glycosylation*, vol.2 (John Wiley & Sons, New York, 1994).
26. Cultures of $2 \times 10^6$ Jurkat cells were grown in 9 mL of media containing varying amounts of a 1 mg/mL solution of tunicamycin in EtOH (4.5, 7.0, 10.0 µL). After 24 hours, 1 mL of a 50 mM solution of ManLev was added. After an additional 48 hours, the cells were washed twice with biotin buffer (0.1% NCS in PBS pH=6.5) and resuspended at a density of $10^7$ cells/mL.

27. V. Piller, F. Piller, M. Fukuda, *J. Biol. Chem.* 265, 9264 (1990).
28. R. Drzeniek, *Histochem. J.* 5, 271 (1973).
29. B. Potvin, T. S. Raju, P. Stanley, *J. Biol. Chem.* 270, 30415
30. G. L. Nicolson, J. Blaustein, M. E. Etzler, *Biochemistry* 13, 196 (1974).
31. Jurkat cells were grown in the presence and absence of ManLev (20 mM) for 72 hours. Cells ($2 \times 10^5$ per sample) were washed with phosphate buffered saline (PBS) (pH 6.5), centrifuged and resuspended in 0.9 mL of sialidase buffer (20 mM HEPES, 140 mM NaCl, pH 6.8). Sialidase (*Clostridium perfringes*, 100 mU in 100 µL) or sialidase buffer (100 µL) was added to the cells and they were incubated at 37° C. for 30 minutes. The cells were centrifuged, washed with PBS (pH=7.4) and resuspended in 0.5 mL of 25 nM FITC labeled *Ricinus communis* agglutinin (FITC-RCA$_{120}$, Sigma). Cells were incubated on ice with the FITC-RCA$_{120}$ for 15 minutes washed twice with PBS (pH=7.4) and analyzed by flow cytometry.
32. The relationship between fluorescence intensity observed by flow cytometry analysis and the number of fluorescent molecules per cell was determined using biotinylated polystyrene beads (Spherotech) with a predetermined number of biotin molecules per bead and with a similar diameter to Jurkat cells.
33. S. Sell, *Human Pathology,* 21, 1003 (1990) and references therein.
34. L. Barbieri, M. G. Battelli, F. Stirpe, *Biochem. Biophys. Acta,* 1154, 237 (1993).
35. J. M. Lord, L. M. Roberts, J. D. Robertus, *FASEB J.,* 8, 201 (1994).
36. A. J. Cumber, et al., *Methods Enzymol.,* 112, 207 (1985).
37. The amino groups of lysine residues on the ricin A chain were modified to present sulfhydryl groups by treatment with 2-iminothiolane (2-IT) as follows. Ricin toxin A chain (RTA) (1.0 mg, Sigma) was exchanged into PBS (pH 8.5) by Sephadex G-25 gel filtration and concentrated to a final volume of 3 mL. A 120 $\mu$L aliquot of a solution of 2-iminothiolane (2-IT) (0.5 M in 0.8 M boric acid, pH 8.0, 50 mM dithiothreitol (DTT)) was added to the RTA solution and incubated for 2 hours at room temperature. Excess 2-IT and DTT were removed-by Sephadex G-25 gel filtration in PBS buffer (pH 7.4). The volume of the RTA-2-IT adduct was reduced to 0.5 mL using a centricon-10 concentrator. The amino groups of lysine residues on avidin were modified to present pyridyldithio groups by reaction with N-succinimidyl 3-(2-pyridyldithio)propionate (SPDP) (Pierce) as follows. A solution of egg-white avidin (Sigma, 2 mg) and SPDP (4 $\mu$L of a 250 mM solution in dimethylsulfoxide) was incubated at room temperature for 1 hour. Excess SPDP was removed by Sephadex G-25 gel filtration and the modified avidin was collected into PBS buffer (pH 7.4). RTA-IT was added to this solution in a 1:1 molar ratio and incubated at room temperature for 18 hours. The 1:1 RTA-avidin conjugate was purified from the reaction by Sephadex G-150 gel filtration and characterized by non-reducing and reducing SDS-PAGE.

38. H. T. Wright and J. D. Robertus, *Archives Biochem. Biophys.*, 256, 280 (1987).

39. S. Ramakrishnan and L. L. Houston, *Cancer Res.*, 44, 201 (1984). Jurkat cells were grown with (or without) ManLev and labeled with biotin-hydrazide in PBS buffer containing 5% NCS as described previously. The cells were washed and resuspended in PBS (pH 7.4, 0.1% NCS) at a density of $5\times10^5$ cells/mL. Cells (100 $\mu$L) were added to 100 $\mu$L of RTA-avidin diluted to various concentrations in PBS with 0.1% NCS. The cells were incubated for 15 minutes at room temperature, and then washed twice to remove excess RTA-avidin. The cells were resuspended in 1.0 mL of media (RPMI-1640 with 5% NCS) and incubated for 3 days. The numbers of living and dead cells were determined by trypan blue staining followed by counting a minimum of 500 cells/sample under a light microscope. Similar results were obtained in three separate experiments.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for making a functionalized glycoconjugate, said method comprising the steps of:

a) contacting a cell with a first monosaccharide comprising a first functional group; and b) incubating said cell under conditions whereby said cell (i) internalizes said first monosaccharide, (ii) biochemically processes said first monosaccharide into a second monosaccharide comprising a second functional group, (iii) conjugates said second monosaccharide to a carrier to form a glycoconjugate comprising a third functional group, and (iv) extracellularly expresses said glycoconjugate to form an extracellular glycoconjugate comprising a fourth, selectively reactive, functional group.

wherein said first functional group is N-linked in said first monosaccharide, said first monosaccharide comprises a ManLev or FucLev, said cell is eukaryotic cell, and said fourth functional group is a covalently or non-covalently reactive group.

2. The method of claim 1 wherein the first monosaccharide is ManLev.

3. The method of claim 1 wherein the first monosaccharide is FucLev.

4. The method of claim 1 wherein the fourth functional group is a covalently reactive group selected from the group consisting of alkenes, alkynes, dienes, thiols, phosphines and boron.

5. The method of claim 1 wherein the fourth functional group is a non-covalently reactive group which is a hapten or a epitope.

6. The method of claim 5 wherein the hapten is biotin and the epitope is dinitrophenol.

7. The method of claim 1 wherein said extracellular glycoconjugate is membrane associated.

8. The method of claim 1 wherein said cell is a eukaryotic cell in situ.

9. A method for forming a product at a cell, said method comprising the steps of:

a) contacting a cell with a first monosaccharide comprising a first functional group; and b) incubating said cell under conditions whereby said cell (i) internalizes said first monosaccharide, (ii) metabolically processes said first monosaccharide into a second monosaccharide comprising a second functional group, (iii) conjugates said second monosaccharide to a carrier to form a glycoconjugate comprising a third functional group, and (iv) extracellularly expresses said glycoconjugate to form an extracellular glycoconjugate comprising a fourth, selectively reactive, functional group, wherein said extracellular glycoconjugate is retained proximate to said cell;

c) contacting said fourth functional group with an agent which selectively reacts with said fourth functional group to form a product;

wherein said first functional group is N-linked in said first monosaccharide, said first monosaccharide comprises a ManLev or FucLev, said cell is a eukaryotic cell, and said fourth functional group is a covalently or non-covalently reactive group.

10. The method of claim 9 wherein the first monosaccharide is ManLev.

11. The method of claim 9 wherein the first monosaccharide is FucLev.

12. The method of claim 9 wherein the fourth functional group is a covalently reactive group selected from the group consisting of alkenes, alkynes, dienes, thiols, phosphines and boron.

13. The method of claim 9, wherein said agent selectively reacts with said fourth functional group by forming non-covalent bonds with said group.

14. The method of claim 13 wherein the non-covalently reactive group is a hapten or an epitope.

15. The method of claim 14 wherein the hapten is biotin and the epitope is dinitrophenol.

16. The method of claim 9 wherein said fourth functional group is boron and the agent which selectively reacts with said fourth functional group to form a product are neutrons and the product is radiation.

17. The method of claim 9, wherein said agent comprises a fifth functional group selected from a hydrazide, dienophile, alpha-bromo amide, avidin, anti-DNP antibodies, UV light and oxygen and wherein the product is hydrazone, a Diels-Alder adduct, thioether, a biotin-avidin complex, a DNP-antibody complex, green light and a peroxy radical, respectively.

18. The method of claim 9, wherein said agent comprises a moiety selected from the group consisting of a toxin, drug, a detectable label, and a chelator.

* * * * *